US005139488A

United States Patent [19]

Klein

[11] Patent Number: 5,139,488

[45] Date of Patent: Aug. 18, 1992

[54] DRENCHING GUN

[75] Inventor: Enrique E. Klein, Buenos Aires, Argentina

[73] Assignee: Syrvet, Inc., Urbandale, Iowa

[21] Appl. No.: 563,988

[22] Filed: Aug. 6, 1990

[51] Int. Cl.[5] .............................................. A61M 5/178

[52] U.S. Cl. .............................................. 604/184

[58] Field of Search ............... 604/236, 247, 231, 223, 604/222, 213, 235, 218, 220, 221, 183, 184, 57-64, 71, 152, 240, 241; 285/184-185, 330, 24, 25

[56] References Cited

U.S. PATENT DOCUMENTS

| | | | |
|---|---|---|---|
| 3,273,805 | 9/1966 | Hall | 285/330 |
| 4,020,838 | 5/1977 | Phillips et al. | 128/223 |
| 4,033,346 | 7/1977 | Phillips et al. | 128/223 |
| 4,245,757 | 1/1981 | Phillips et al. | 222/43 |
| 4,359,050 | 11/1982 | Reynolds | 128/223 |
| 5,037,399 | 8/1991 | Reichert et al. | 604/184 |

FOREIGN PATENT DOCUMENTS

| | | | |
|---|---|---|---|
| 0014330 | 9/1929 | Australia | 604/236 |

OTHER PUBLICATIONS

Syrvet Inc., Accurate and Sturdy Veterinary Instruments, Catalog, pp. 6-8.

*Primary Examiner*—C. Fred Rosenbaum
*Assistant Examiner*—M. Mendez
*Attorney, Agent, or Firm*—Zarley, McKee, Thomte, Voorhees & Sease

[57] ABSTRACT

The drenching gun of the present invention comprises a cylinder having an outlet opening in one end. A plunger is mounted within the cylinder and is adapted to reciprocate therein. A nozzle is attached to the outlet end of the cylinder and includes a one-way valve which is fitted within a tube in the outlet end of the chamber. The valve is integral with the nozzle. All of the forces between the cylinder and the nozzle are borne by metal parts, and a pair of pins are provided on the nozzle for cooperating with axial slots in the cylinder to hold the nozzle against rotational movement with respect to the cylinder.

4 Claims, 2 Drawing Sheets

DRENCHING GUN

BACKGROUND OF THE INVENTION

This invention relates to a drenching gun, and specifically a drenching gun for administering fluids to livestock.

Drenching guns are used to deliver a dosage of drench or fluid usually to the mouth of a beast, such as a cow or horse. Often times during the administering of the drench to the animal, the drenching gun is subjected to stress resulting from the animal tossing its head or other movement of the animal.

Present drenching guns comprise a handle and cylinder adapted to deliver a quantity of drench solution to a nozzle at the end of the device. The nozzle has one end inserted in an outlet end of the cylinder, and includes a discharge end at the end of a long nozzle tube. The nozzle tube is usually bent at the discharge end to a desired angle for administering the fluid to the animal. Considerable stress occurs at the connection between the nozzle and the cylinder, and this often results in breakage of the cylinder.

Present devices utilize two sets of valves, both of which are contained within the cylinder. These two valves in present devices are separate from and not part of the nozzle tube which is attached to the cylinder.

Therefore, a primary object of the present invention is to provide an improved drenching gun.

A further object of the present invention is the provision of an improved drenching gun which provides more substantial attachment of the nozzle to the handle and cylinder of the device.

A further object of the present invention is the provision of a drenching gun which includes means for preventing the rotation of the nozzle relative to the cylinder during the use of the device.

A further object of the present invention is the provision of a drenching gun having a nozzle tube which has incorporated therein an integral valve for insertion into the cylinder of the drenching gun.

A further object of the present invention is the provision of an improved drenching gun which is sturdier and more capable of withstanding forces encountered during the tossing of the animal's head or other movement of the animal.

A further object of the present invention is the provision of an improved drenching gun which is economical to manufacture, durable in use, and efficient in operation.

SUMMARY OF THE INVENTION

The present invention comprises a cylinder having an inlet end and an outlet end. An outlet opening is provided in the outlet end of the cylinder. Within the cylinder is a plunger which is adapted to slide within the cylinder in a piston-like manner. A cylinder chamber is created between the plunger and the outlet end of the cylinder barrel.

Within the plunger is a plunger chamber which is adapted to be connected to a source of drenching fluid. Also within the plunger is a first one-way valve which permits fluid to pass from the plunger chamber outwardly from the plunger into the cylinder chamber. The one-way valve prevents fluid from flowing backward from the cylinder chamber into the plunger chamber.

An important feature of the present invention is a novel nozzle means which has an inlet and outlet end. Integrally formed on the inlet end of the nozzle is a one-way valve which is adapted to be inserted into the outlet end of the cylinder and which is adapted to permit fluid to flow from the cylinder chamber through the outlet end of the cylinder and into the nozzle. The one-way valve attached to the nozzle, however, is adapted to prevent reverse flow of fluid from the nozzle back into the cylinder chamber.

The nozzle also includes an enlarged shank which is adapted to fit within the outlet end of the cylinder. Thus, when the nozzle is attached to the cylinder, it includes both the integral valve and the shank inserted within the outlet end of the cylinder. A locking nut fits over the juncture between the nozzle and the cylinder so as to secure the two together.

Another novel feature of the present invention is the utilization of a pair of pins on the nozzle which are adapted to fit within various axially extending slots located on the outlet end of the cylinder. Thus, it is possible to position the nozzle in a number of rotational positions with respect to the cylinder. The nozzle can then be attached to the cylinder so that it will not rotate relative to the cylinder.

Another important feature of the present invention is the fact that the cylinder is made of a metallic outer shell and a plastic inner shell. The connection between the nozzle and the cylinder is all metal so that the metal bears the forces between the nozzle and the cylinder. The valve on the nozzle, however, is fitted within a plastic tube which comprises part of the inner plastic shell of the cylinder. The valve and the tube, however, do not bear any of the bending forces or other forces which result between the nozzle and the cylinder as a result of an animal tossing its head or otherwise moving. This prevents breakage of the plastic, even though the integral valve of the nozzle is positioned within the plastic.

DETAILED DESCRIPTION OF THE PREFERRED EMBODIMENT

Figure 1:
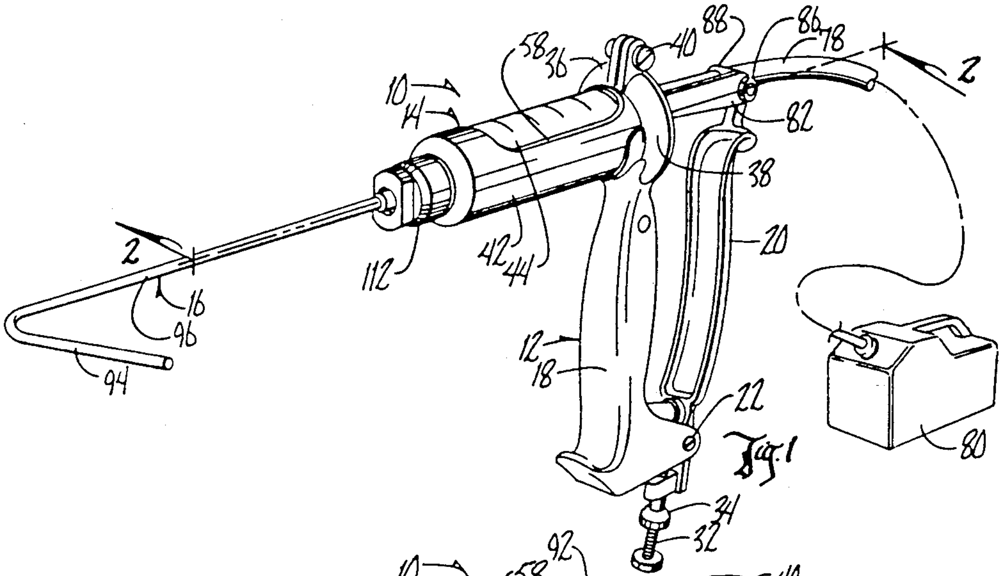
FIG. 1 is a perspective view of the drenching gun of the present invention.

Referring to the drawings, the numeral 10 generally designates the drenching gun of the present invention. Drenching gun 10 comprises a handle 12, a cylinder 14, and a nozzle 16.

Handle 12 is comprised of a fixed grip 18 and a movable grip 20 which are pivoted about the axis provided by pivot 22. Attached to the lower end of movable grip 20 is a fixed link 24 which is attached by means of a spring to a spring pin 28 within fixed grip 18. This spring causes the movable grip 20 to be spring biased in a counterclockwise direction about the pivotal axis 22 as viewed in FIG. 2.

Attached to the bottom of movable grip 20 is a bottom member 30 which has an adjusting screw 32 threaded therethrough. A lock nut 34 is also threaded upon adjustment screw 32. By threading adjustment screw upwardly and downwardly within bottom member 30, it is possible to adjust the position of movable grip 20 relative to fixed grip 12. The end of screw 32 engages the bottom of fixed grip 12 and limits the counterclockwise movement of the movable grip 20 with respect thereto.

The upper end of fixed grip 12 includes a pair of fixed yoke members 36, 38 which are joined at their upper ends by means of a screw 40. The yoke members 36, 38 embrace the rear end of a metal cylindrical housing 42. By tightening screw 40, it is possible to attach the metal cylindrical housing 42 to the fixed grip 12.

Within metal cylindrical housing 42 is a plastic inner housing 44 which is cylindrical in shape. The inner end 46 of metal housing 42 is fitted within and embraced by the yoke members 36, 38. The metal housing 42 also includes a barrel portion 48 and an outlet tube 50 which includes threads 52 on the outer surface thereof. A bore 54 extends through the metal outer tube of the metal cylinder 42. Metal cylinder 42 also includes an inner threaded counter bore 56 which is provided on the inner end of bore 54. In the upper portion of metal cylinder 42 is a window 58. Plastic cylinder 44 includes a barrel portion 60 and a threaded tube 62 which is threaded within the threaded counter bore 56 of metal cylinder 42. The threaded connection between threaded tube 62 and threaded counter bore 56 secures the metal cylinder and the plastic cylinder together in the position shown in FIGS. 2 and 3. Extending within the threaded tube 62 is a plastic bore 64 which provides essentially a smooth continuation of the metal bore 54 of the metal housing 42.

Slidably mounted within the interior of plastic cylinder 44 is a plunger body 68 which is adapted to slide longitudinally in a piston-like fashion. Plunger body 68 includes a plunger cavity 70 therein and a one-way valve 72. Valve 72 is held in position by means of a screw 74.

An inlet passageway 76 provides communication from the exterior of plunger body 68 to the interior of the plunger cavity 70. A fluid supply tube 78 is attached to inlet passageway 76 at one end, and at the other end is connected to a fluid supply tank.

A plunger link 82 is attached to the plunger body 68 by means of a forward link pin 84. The rear end of plunger link 82 is pivotally attached to the upper end of movable grip 20 by means of a rear link pin 86. Plunger link 82 includes a tube holder 88 which is adapted to surround and hold the tube 78 during reciprocating movement of the link and the plunger body 68.

A plurality of seals 90 are provided around the perimeter of plunger body 68 so as to provide sealing engagement between the plunger body 68 and the interior of the plastic cylinder 44. Formed between the plunger 66 and the threaded tube 62 of cylinder 44 is a cylinder chamber 92 which enlarges when plunger 66 moves to the right as viewed in FIG. 3 and which becomes smaller as the plunger 66 moves to the left as viewed in FIG. 3.

Nozzle 16 includes an angled end 94, a straight portion 96, and a nozzle valve 98. Nozzle valve 98 is formed by means of a circular flange 100 and a circular elastomeric valve member 102 as well as a radial port 104 which leads to the interior of the nozzle 16. An O-ring 106 provides a seal of the nozzle valve 98 with the interior of the metal bore 54 of cylinder 42. It should be noted, however, that the elastomeric valve member 102 bears against the inner plastic surface 64 of the inner plastic member 44.

An enlarged shank 108 is formed immediately adjacent the nozzle valve 98, and is adapted to fit snugly within the metal bore 54 so as to prevent movement of the nozzle 16 relative to the metal cylinder 42. It should be noted that shank 108 engages only the metal portion 54 and does not engage the plastic bore 64. This prevents forces being applied to the plastic which can result in cracking or breaking of the plastic. It should be noted that the plastic is engaged only by the elastomeric member 102 and does not bear the brunt of any forces between the nozzle 16 and the cylinder 42.

Figure 3:
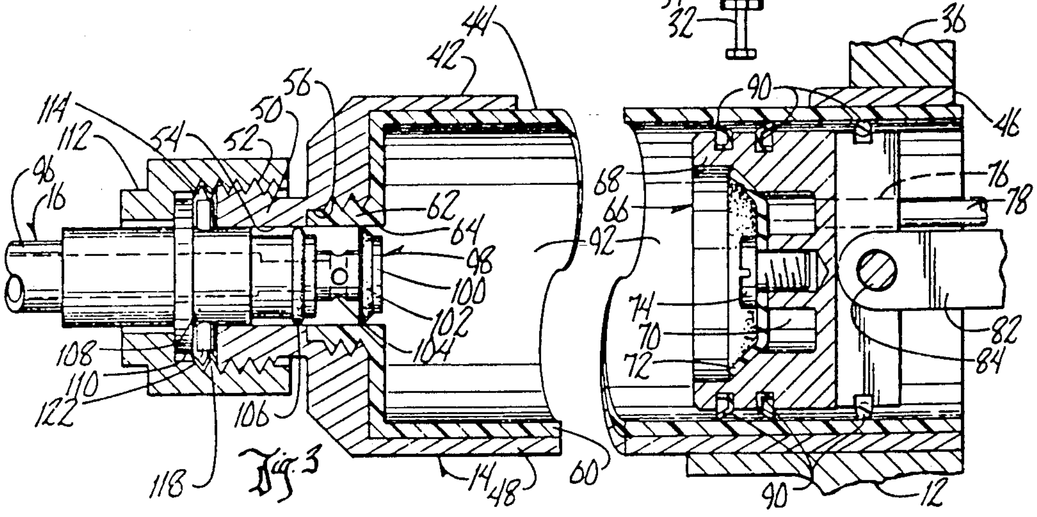
FIG. 3 is an enlarged detailed view of the cylinder, shown in section.
Figure 4:
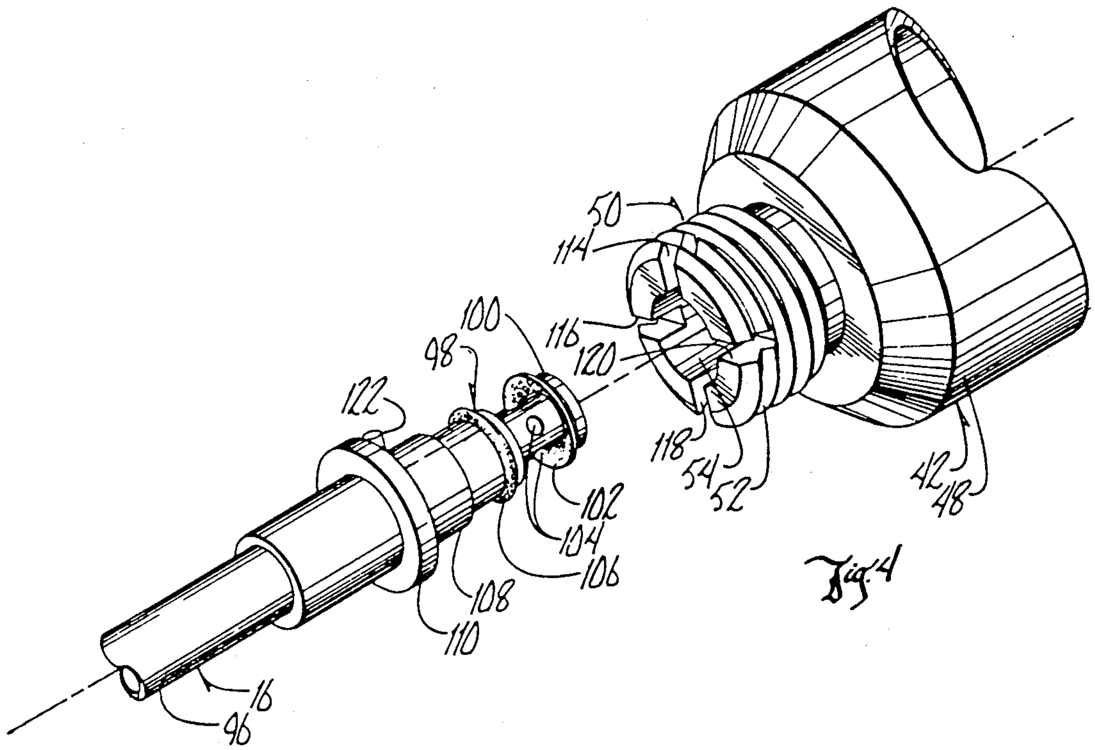
FIG. 4 is a detailed perspective view of the inlet end of the nozzle and the outlet end of the cylinder.

An annular flange 110 is provided adjacent the enlarged shank 108 and is adapted to abut against the axial end of the metal tube 50 of cylinder 44 in the manner shown in FIG. 3. As can best be seen in FIG. 4, a plurality of axial slots 114, 116, 118, and 120 are provided in the metal outlet tube 50, and these are adapted to receive a pair of radially extending pins 122 which are fixed to the enlarged shank 108 adjacent the flange 110.

To attach the nozzle 16 to the metal cylinder 42, one merely inserts the valve 98 and the shank 108 into the cylinder as shown in FIG. 3, with the elastomeric member 102 of valve 98 engaging the plastic bore 64, and with the enlarged shank 108 snugly fitted within the metal bore 54. The pins 122 are inserted and extend within two of the slots 114, 116, 118, and 120. The desired rotational position of the nozzle can be achieved by rotating the nozzle to have the pins 122 located within different pairs of slots. Once the nozzle is inserted into the cylinder, a locking nut 112 is threaded over the threads 52 on the outer surface of outlet tube 50, and this locking nut then holds the nozzle securely attached to the metal cylinder 42. It can be seen that all of the forces between the nozzle 16 and the metal cylinder 42 are borne by engaging metal parts, and the valve 98 is prevented from bearing any forces between the nozzle and the cylinder. Similarly, the plastic tube 62 does not bear any of the forces between the nozzle and the cylinder, thereby minimizing the likelihood of damage either to the valve 98 or to the plastic bore 64. This ensures that the valve 98 will function properly during use.

In operation, the tube 78 is connected to a source of drenching fluid 80. The bent portion 94 of nozzle 16 is inserted into the animals mouth, and the grips 18, 20 are grasped by the operator's hands. The operator then can squeeze the grips together so as to cause plunger body 68 to move towards the outlet bore 64 thereby compressing the space within cylinder chamber 92. Fluid within the cylinder chamber 92 is thus forced past valve member 102 (which deflects in response to this pressure) and into the radial bore 94 and then outwardly through the nozzle 16 into the animal's mouth.

Figure 2:
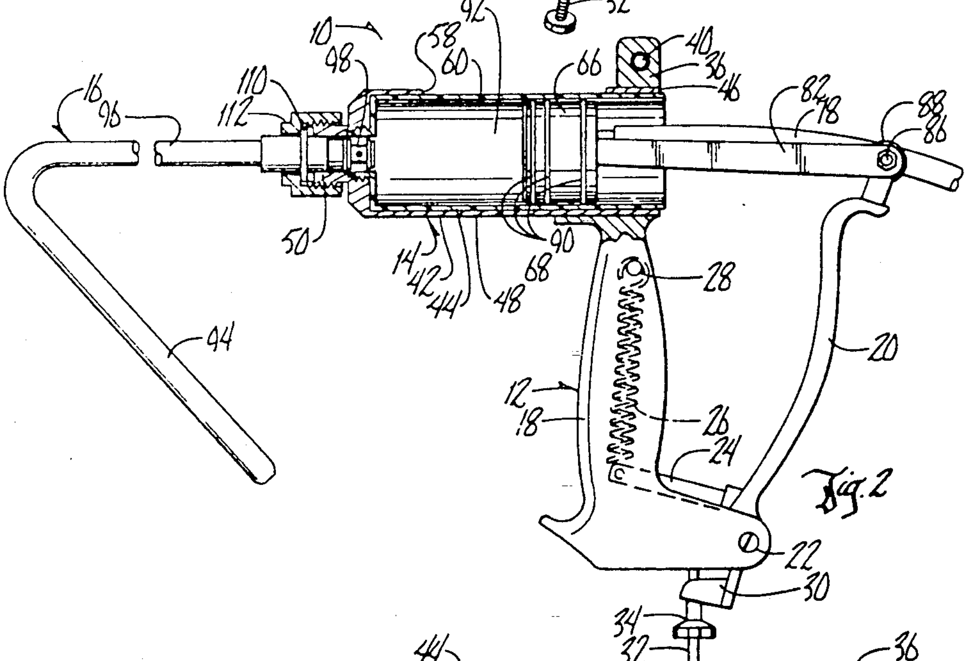
FIG. 2 is a sectional view taken along line 2—2 of FIG. 1.

The operator then relaxes the grip between movable and fixed grips 18, 20 so as to permit the spring 26 to cause the grip 20 to move to the right as viewed in FIGS. 2 and 3. This causes the plunger 66 to move to the right thereby creating a vacuum within cylinder chamber 92. The vacuum causes fluid within tube 78 to be drawn from the tube into the plunger chamber 70 and outwardly past elastomeric valve member 72 into the cylinder chamber 92. The elastomeric member 72 deflects so as to permit fluid to flow from the plunger chamber 70 into the cylinder chamber 92. However, upon a reversal of the movement of the plunger 66 so that it moves in the direction to the left as viewed in FIG. 3, the valve 72 closes and prevents fluid from reversing its flow and passing from the cylinder chamber 92 into the plunger chamber 70.

Because the valve 98 does not bear any of the forces between the tube 16 and the cylinder 42, the valve remains in good operating order. Similarly, the plastic of the inner cylinder 44 does not bear any forces between the cylinder 42 and the nozzle 16, and therefore is less likely to be damages during movement of the animal's head or during other forces being applied to the device. Thus, it can be seen that the device accomplishes at least all of its stated objectives.

I claim:

1. A drenching gun comprising:

an elongated cylinder comprising an inner plastic housing and an outer metal housing surrounding said plastic housing;

said inner plastic housing having an elongated plastic barrel portion containing a cylindrical plastic barrel bore therein, said barrel bore having first and second opposite ends;

said inner plastic housing having a plastic tube portion forming a plastic tube bore smaller in cross section than said plastic barrel bore end extending axially from said first end of said plastic barrel bore, said plastic tube portion having a distal end extending axially away from said plastic barrel portion;

said outer metal housing having a metal tube portion forming a metal tube bore having an inner axial end and an outer axial end;

said plastic tube portion extending partially within said inner axial end of said metal tube bore;

a plunger mounted within said plastic barrel bore for reciprocating axial movement therein toward and away from said first end of said plastic barrel tube so as to form a variably sized barrel chamber within said plastic barrel bore between said plunger and said first end of said barrel bore;

said plunger containing a plunger chamber adapted to be connected to a source of fluid;

a first one way valve means within said plunger for permitting fluid to pass from said plunger chamber to said barrel chamber, said one way valve means preventing fluid flow from said cylinder chamber to said plunger chamber;

nozzle means having an outlet end and an inlet end, said inlet end having a second one way valve fixedly attached thereto for permitting fluid flow from said inlet end to said outlet end of said nozzle and for preventing fluid flow from said outlet end to said inlet end of said nozzle, said nozzle means including a nozzle shank adjacent said second one way valve means;

said second valve means protruding within said plastic tube bore of said inner plastic housing and said nozzle shank protruding within said metal tube bore of said outer metal housing adjacent said outer axial end of said metal tube bore, said nozzle shank being in contact with said metal tube of said outer metal housing and being free from contact with said plastic tube of said inner plastic housing;

securing means detachably securing said nozzle shank within said metal tube bore of said metal tube.

2. A drenching gun according to claim 1 wherein said securing means comprises a flange fixed to said nozzle means and engaging said metal tube portion outside and adjacent said outer axial end of said metal tube bore, and a collar surrounding said metal tube portion and engaging said flange to secure said flange to said metal tube portion.

3. A drenching gun according to claim 1 wherein said metal tube portion of said outer metal housing includes at least one axially extending slot adjacent said outer axial end of said metal tube bore, said nozzle means having at least one pin extending radially outwardly with respect to said metal tube bore and protruding within said slot to prevent relative rotation between said nozzle and cylinder.

4. A drenching gun according to claim 3 wherein said pin is free from engagement with any part of said inner plastic housing.

* * * * *